(12) United States Patent
Sekar et al.

(10) Patent No.: US 7,888,561 B2
(45) Date of Patent: Feb. 15, 2011

(54) UBIQUITIN REGULATORY NUCLEIC ACIDS, VECTORS, AND METHODS OF USING SAME

(75) Inventors: Vaithilingam Sekar, Ames, IA (US); Carol Lewnau, Ames, IA (US); Janell Eby, Ames, IA (US); Brad Atchinson, Ames, IA (US); Bruce Held, Ames, IA (US)

(73) Assignee: MS Technologies, LLC, West Point, IA (US)

( * ) Notice: Subject to any disclaimer, the term of this patent is extended or adjusted under 35 U.S.C. 154(b) by 96 days.

(21) Appl. No.: 12/480,275

(22) Filed: Jun. 8, 2009

(65) Prior Publication Data

US 2010/0199377 A1    Aug. 5, 2010

Related U.S. Application Data

(60) Continuation of application No. 12/124,758, filed on May 21, 2008, now abandoned, which is a division of application No. 11/773,861, filed on Jul. 5, 2007, now Pat. No. 7,393,948.

(60) Provisional application No. 60/909,846, filed on Apr. 3, 2007, now abandoned.

(51) Int. Cl.
| A01H 5/00 | (2006.01) |
| C12N 15/82 | (2006.01) |
| C12N 15/63 | (2006.01) |
| C12N 5/14 | (2006.01) |
| C07H 21/04 | (2006.01) |

(52) U.S. Cl. .................... 800/295; 800/278; 435/320.1; 435/468; 536/24.1

(58) Field of Classification Search ........................ None
See application file for complete search history.

(56) References Cited

U.S. PATENT DOCUMENTS

| 5,510,474 A | 4/1996 | Quail et al. |
| 5,614,399 A | 3/1997 | Quail et al. |
| 6,020,190 A | 2/2000 | Quail et al. |
| 6,054,574 A | 4/2000 | Quail et al. |
| 6,977,325 B2 | 12/2005 | Jilka et al. |
| 2004/0031072 A1 | 2/2004 | La Rosa et al. |

OTHER PUBLICATIONS

Bao-Sen et al., NCBI, GenBank, Sequence Accession No. D28123, Published Jan. 25, 2003.*
Hernandez-Garcia et al. (2009) Plant Cell Rep. 28(d): 837-49.
Chiera et al. "Isolation of two highly active soybean (Glycine max (L.) Merr.) promoters and their characterization using a new automated image collection and analysis system" Plant Cell Rep. (2007) 26:1501-1509.
Finer et al. "Characterization of soybean promoters through evaluation of GFP expression in transgenic soybean" the 11th biennial conference on the Molecular & Cellular Biology of the Soybean, abstract, Aug. 5-8, 2006, University of Nebraska, Lincoln NE.
Xia et al. "Nucleotide sequence of a soybean (Glycine mas L. Merr.) ubiquitin gene" Plant Physiol. (1994) 104:805-806.
Xia et al. "Glycine max Subi-1 gene for ubiquitin, complete cds" Genbank accession No. D16248.1 (2003).
Bao-Sen et al. "Glycine max SUBI-3 gene for ubiquitin, complete cds." Genbank accession No. D28123.1 (2003).
Mogen et al. (1990) Plant Cell., vol. 2, 1261-1272.

* cited by examiner

*Primary Examiner*—Vinod Kumar
(74) *Attorney, Agent, or Firm*—Patricia A. Sweeny

(57) ABSTRACT

The invention is directed to a soybean polyubiquitin promoter, polyubiquitin terminator, sequences which hybridize to same and functional fragments thereof. The regulatory element of the invention provide improved expression in plants of operably linked nucleotide sequences. Expression vectors with the regulatory element is the subject of the invention, which may further include an operably linked nucleotide sequence. The invention is further directed to transformed plant tissue including the nucleotide sequence and to transformed plants and seeds thereof. The regulatory element is useful for driving a nucleotide sequence, for example a gene, or antisense expression or the like for the purpose of imparting agronomically useful traits such as, but not limited to, increase in yield, disease resistance, insect resistance, herbicide tolerance, drought tolerance and salt tolerance in plants.

20 Claims, 2 Drawing Sheets

Figure 1A

*Glycine max* polyubiquitin promoter sequence (gmubipro) wih restriction/Kozak sites:

```
EcoRI    SbfI    ApaI
GAATTCCTGCAGGGCCCAATATAACAACGACGTCGTAACAGATAAAGCGAAGCTTGAAGGTGCATGTGACTCCG
TCAAGATTACGGAACCGCCAACTACCACGCAAATTGCAATTCTCAATTTCCTAGAAGGACTCTCCGAAAATGCA
TCCAATACCAAATATTACCCGTGTCATAGGCACCAAGTGACACCATACATGAACACGCGTCACAATATGACTGG
AGAAGGGTTCCACACCTTATGCTATAAAACGCCCCACACCCCTCCTCCTTCCTTCGCAGTTCAATTCCAATATA
TTCCATTCTCTCTGTGTATTTCCCTACCTCTCCCTTCAAGGTTAGTCGATTTCTTCTGTTTTTCTTCTTCGTTC
TTTCCATGAATTGTGTATGTTCTTTGATCAATACGATGTTGATTTGATTGTGTTTTGTTTGGTTTCATCGATCT
TCAATTTTCATAATCAGATTCAGCTTTTATTATCTTTACAACAACGTCCTTAATTTGATGATTCTTTAATCGTA
GATTTGCTCTAATTAGAGCTTTTTCATGTCAGATCCCTTTACAACAAGCCTTAATTGTTGATTCATTAATCGTA
GATTAGGGCTTTTTTCATTGATTACTTCAGATCCGTTAAACGTAACCATAGATCAGGGCTTTTTCATGAATTAC
TTCANATCCGTTAAACAACAGCCTTATTTTTATACTTCTGTGGTTTTTCAAGAAATTGTTCAGATCCGTTGAC
AAAAAGCCTTATTCGTTGATTCTATATCGTTTTTCGAGAGATATTGCTCAGATCTGTTAGCAACTGCCTTGTTT
GTTGATTCTATTGCCGTGGATTAGGGTTTTTTTTCACGAGATTGCTTCAGATCCGTACTTAAGATTACGTAATG
GATTTTGATTCTGATTTATCTGTGATTGTTGACTCGACAGGCCGCCGAGCTC
                                      Kozak    SacI
```

Figure 1B

*Glycine max* polyubiquitin 911bp promoter sequence (gmubipro):

AATATAACAACGACGTCGTAACAGATAAAGCGAAGCTTGAAGGTGCATGTGA
CTCCGTCAAGATTACGGAACCGCCAACTACCACGCAAATTGCAATTCTCAAT
TTCCTAGAAGGACTCTCCGAAAATGCATCCAATACCAAATATTACCCGTGTCA
TAGGCACCAAGTGACACCATACATGAACACGCGTCACAATATGACTGGAGAA
GGGTTCCACACCTTATGCTATAAAACGCCCCACACCCCTCCTCCTTCCTTCGC
AGTTCAATTCCAATATATTCCATTCTCTCTGTGTATTTCCCTACCTCTCCCTTC
AAGGTTAGTCGATTTCTTCTGTTTTTCTTCTTCGTTCTTTCCATGAATTGTGTAT
GTTCTTTGATCAATACGATGTTGATTTGATTGTGTTTTGTTTGGTTTCATCGAT
CTTCAATTTTCATAATCAGATTCAGCTTTTATTATCTTTACAACAACGTCCTTA
ATTTGATGATTCTTTAATCGTAGATTTGCTCTAATTAGAGCTTTTTCATGTCAG
ATCCCTTTACAACAAGCCTTAATTGTTGATTCATTAATCGTAGATTAGGGCTT
TTTTCATTGATTACTTCAGATCCGTTAAACGTAACCATAGATCAGGGCTTTTT
CATGAATTACTTCANATCCGTTAAACAACAGCCTTATTTTTATACTTCTGTG
GTTTTTCAAGAAATTGTTCAGATCCGTTGACAAAAAGCCTTATTCGTTGATTC
TATATCGTTTTTCGAGAGATATTGCTCAGATCTGTTAGCAACTGCCTTGTTTGT
TGATTCTATTGCCGTGGATTAGGGTTTTTTTTCACGAGATTGCTTCAGATCCGT
ACTTAAGATTACGTAATGGATTTTGATTCTGATTTATCTGTGATTGTTGACTCG
ACAG

Figure 2A

*Glycine max* polyubiquitin terminator sequence with restriction sites(gmubiter):

```
XbaI
TCTAGAGCTCGTTGTGTAATGTTGGATGTGTTCCCAAAACATTTGAAGAACTTTGATGTTTAATGGGTCTGTAA
TAATGTCCCTTGAAAATAAGTTCGGTTTGTGTTGAACTCAATTGTGTCCCATTAATAATAGTACTCTAATATCC
CACCTACGTTTGTTATGAATGTGTGAAATATGAAATGATTAATTGTCATATCGTGTTGTTTTAATTTGTTCTGA
ATTGGCTAGAGGGGACTTAATATGGATTTTTTATTCGATTTGTGTGGTCTTCCATGCTTGTCATGAAGGAAAAA
CAGGGATGAGTTGTGTGAAGGATGGTGATCATCCTGCAGGCTCGAG
                                  SbfI    XhoI
```

Figure 2B

*Glycine max* polyubiquitin 322bp terminator sequence (gmubiter):

GCTCGTTGTGTAATGTTGGATGTGTTCCCAAAACATTTGAAGAACTTTGATGT
TAATGGGTCTGTAATAATGTCCCTTGAAAATAAGTTCGGTTTGTGTTGAACT
CAATTGTGTCCCATTAATAATAGTACTCTAATATCCCACCTACGTTTGTTATG
AATGTGTGAAATATGAAATGATTAATTGTCATATCGTGTTGTTTTAATTTGTT
CTGAATTGGCTAGAGGGGACTTAATATGGATTTTTTATTCGATTTGTGTGGTC
TTCCATGCTTGTCATGAAGGAAAAACAGGGATGAGTTGTGTGAAGGATGGTG
ATCAT

SEQUENCE LISTING

```
<160> NUMBER OF SEQ ID NOS: 8

<210> SEQ ID NO 1
<211> LENGTH: 940
<212> TYPE: DNA
<213> ORGANISM: Glycine max
<220> FEATURE:
<221> NAME/KEY: modified_base
<222> LOCATION: (671)
```

<223> OTHER INFORMATION: a, c, g, t, unknown or other

<400> SEQUENCE: 1

```
gaattcctgc agggcccaat ataacaacga cgtcgtaaca gataaagcga agcttgaagg        60
tgcatgtgac tccgtcaaga ttacggaacc gccaactacc acgcaaattg caattctcaa       120
tttcctagaa ggactctccg aaaatgcatc caataccaaa tattacccgt gtcataggca       180
ccaagtgaca ccatacatga acacgcgtca caatatgact ggagaagggt tccacacctt       240
atgctataaa acgccccaca cccctcctcc ttccttcgca gttcaattcc aatatattcc       300
attctctctg tgtatttccc tacctctccc ttcaaggtta gtcgattct  tctgttttc        360
ttcttcgttc tttccatgaa ttgtgtatgt tctttgatca atacgatgtt gatttgattg       420
tgttttgttt ggtttcatcg atcttcaatt ttcataatca gattcagctt ttattatctt       480
tacaacaacg tccttaattt gatgattctt taatcgtaga tttgctctaa ttagagcttt       540
ttcatgtcag atccctttac aacaagcctt aattgttgat tcattaatcg tagattaggg       600
cttttttcat tgattacttc agatccgtta aacgtaacca tagatcaggg cttttcatg        660
aattacttca natccgttaa acaacagcct tatttttat acttctgtgg ttttcaaga         720
aattgttcag atccgttgac aaaaagcctt attcgttgat tctatatcgt ttttcgagag       780
atattgctca gatctgttag caactgcctt gtttgttgat tctattgccg tggattaggg       840
ttttttttca cgagattgct tcagatccgt acttaagatt acgtaatgga ttttgattct       900
gatttatctg tgattgttga ctcgacaggc cgccgagctc                             940
```

<210> SEQ ID NO 2
<211> LENGTH: 911
<212> TYPE: DNA
<213> ORGANISM: Glycine max
<220> FEATURE:
<221> NAME/KEY: modified_base
<222> LOCATION: (654)
<223> OTHER INFORMATION: a, c, g, t, unknown or other

<400> SEQUENCE: 2

```
aatataacaa cgacgtcgta acagataaag cgaagcttga aggtgcatgt gactccgtca        60
agattacgga accgccaact accacgcaaa ttgcaattct caatttccta gaaggactct       120
ccgaaaatgc atccaatacc aaatattacc cgtgtcatag gcaccaagtg acaccataca       180
tgaacacgcg tcacaatatg actggagaag ggttccacac cttatgctat aaaacgcccc       240
acacccctcc tccttccttc gcagttcaat tccaatatat tccattctct ctgtgtattt       300
ccctacctct cccttcaagg ttagtcgatt tcttctgttt ttcttcttcg ttctttccat       360
gaattgtgta tgttctttga tcaatacgat gttgatttga ttgtgttttg tttggtttca       420
tcgatcttca attttcataa tcagattcag cttttattat ctttacaaca acgtccttaa       480
tttgatgatt cttttaatcgt agatttgctc taattagagc ttttttcatgt cagatccctt      540
tacaacaagc cttaattgtt gattcattaa tcgtagatta gggcttttt  cattgattac       600
ttcagatccg ttaaacgtaa ccatagatca gggcttttc atgaattact tcanatccgt       660
taaacaacag ccttattttt tatacttctg tggtttttca agaaattgtt cagatccgtt       720
gacaaaaagc cttattcgtt gattctatat cgttttttcga gagatattgc tcagatctgt       780
tagcaactgc cttgtttgtt gattctattg ccgtggatta gggttttttt tcacgagatt       840
gcttcagatc cgtacttaag attacgtaat ggattttgat tctgatttat ctgtgattgt       900
tgactcgaca g                                                           911
```

<210> SEQ ID NO 3
<211> LENGTH: 342
<212> TYPE: DNA
<213> ORGANISM: Glycine max

<400> SEQUENCE: 3

```
tctagagctc gttgtgtaat gttggatgtg ttcccaaaac atttgaagaa ctttgatgtt      60
taatgggtct gtaataatgt cccttgaaaa taagttcggt ttgtgttgaa ctcaattgtg     120
tcccattaat aatagtactc taatatccca cctacgtttg ttatgaatgt gtgaaatatg     180
aaatgattaa ttgtcatatc gtgttgtttt aatttgttct gaattggcta gaggggactt     240
aatatggatt ttttattcga tttgtgtggt cttccatgct tgtcatgaag gaaaaacagg     300
gatgagttgt gtgaaggatg gtgatcatcc tgcaggctcg ag                        342
```

<210> SEQ ID NO 4
<211> LENGTH: 322
<212> TYPE: DNA
<213> ORGANISM: Glycine max

<400> SEQUENCE: 4

```
gctcgttgtg taatgttgga tgtgttccca aaacatttga agaactttga tgtttaatgg      60
gtctgtaata atgtcccttg aaaataagtt cggtttgtgt tgaactcaat tgtgtcccat     120
taataatagt actctaatat cccacctacg tttgttatga atgtgtgaaa tatgaaatga     180
ttaattgtca tatcgtgttg ttttaatttg ttctgaattg gctagagggg acttaatatg     240 gatttttat tcgatttgtg tggtcttcca tgcttgtcat gaaggaaaaa cagggatgag     300
ttgtgtgaag gatggtgatc at                                              322
```

<210> SEQ ID NO 5
<211> LENGTH: 39
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 5

```
gaattcctgc agggcccaat ataacaacga cgtcgtaac                             39
```

<210> SEQ ID NO 6
<211> LENGTH: 40
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 6

```
gagctcggcg gcctgtcgag tcaacaatca cagataaatc                            40
```

<210> SEQ ID NO 7
<211> LENGTH: 44
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 7

```
ctcgagcctg caggatgatc accatccttc acacaactca tccc                       44
```

```
<210> SEQ ID NO 8
<211> LENGTH: 41
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 8
ctcgagcctg cagggaattc gaaggatgat caccatcctt c                            41
```

UBIQUITIN REGULATORY NUCLEIC ACIDS, VECTORS, AND METHODS OF USING SAME

REFERENCE TO RELATED APPLICATIONS

This application is a continuation of previously filed and application U.S. Ser. No. 12/124,758, filed May 21, 2008, now abandoned, which is a divisional of previously filed application U.S. Ser. No. 11/773,861, filed Jul. 5, 2007, now U.S. Pat. No. 7,393,948, issued Jul. 1, 2008, which claims priority to previously filed application U.S. Ser. No. 60/909,846, filed Apr. 3, 2007, now abandoned, the contents of each are incorporated by reference in their entirety.

BACKGROUND OF THE INVENTION

The expression of a heterologous nucleotide sequence in a plant cell is impacted by regulatory nucleic acids. Promoters and terminators are two types of regulatory elements that impact expression of such operably linked sequences. Promoters are vital molecular tools that have been applied widely in plant biotechnology to control the expression of introduced genes. A promoter is a nucleic acid sequence to which RNA polymerase must bind if it is to transcribe the linked gene into messenger RNA and ultimately produce protein. A promoter may affect a structural gene operationally associated with the promoter in different ways. For example, it may enhance or repress expression of an associated structural gene, subject that gene to developmental regulation, or contribute to the tissue-specific regulation of that gene. There are different types of promoters used dependent upon the function desired. Constitutive promoters provide for expression throughout all tissues of the plant, where tissue preferred promoters will express at a higher rate in a (or a few) select tissue of the plant. Inducible promoters are those which induce the regulatory affect of the promoter in response to a stimulus, which can be, for example, chemical, temperature, stress, wounding or other stimuli. The linked nucleotide sequence can perform any of a wide variety of functions desired, whether it is repressing or initiating expression of a trait or protein of interest, providing for over-expression, modifying metabolic and developmental pathways within the plant tissue, or the like.

Several promoters of plant and plant pathogen (bacterial and viral) origin have been used to direct transgene expression in plants. Prominent examples include the French bean beta-phaseolin promoter (Bustos et al., 1989), the mannopine synthase promoter of *Agrobacterium tumefaciens* (Leung et al., 1991), and the 35S promoter of cauliflower mosaic virus (Guilley et al., 1982). These and several other promoters in widespread use in plants were originally developed and utilized in dicot species. Despite the desire to identify constitutive promoters capable of driving a relatively high level of gene expression in most tissues of the plant, there remain few to choose from and there is an ongoing need to identify promoters for use in expressing linked sequences.

Terminator sequences also play an important role in regulation of gene expression. The 3' terminus of an isolated nucleotide sequence is the site as which transcription stops. A terminator region can be native with the promoter used, can be native with the linked heterologous sequences or derived from another source.

Ubiquitin is a 76 amino acid polypeptide found in all eukaryotes and has been studied for its role in a wide range of cellular functions. Promoters of the ubiquitin gene have been isolated. For example, in U.S. Pat. Nos. 5,510,474, 5,614,399, 6,054,574 and 6,020,190 to Quail is described ubiquitin promoters which include a heat shock element and intron. Jilka et al. describe another maize ubiquitin type promoter at U.S. Pat. No. 6,977,325. Xia et al. identified a soybean genomic clone containing a ubiquitin gene (Xia et al., 1994). Analysis of the nucleotide sequence of this clone revealed the presence of a translational start site, a translational stop codon, a 915-bp open reading frame encoding polyubiquitin (arranged as three tandem 228-bp head-to-tail repeats and a fourth terminal repeat containing 231 bp), a putative polyadenylation signal motif. However, no transcription initiation site was identified. These sequences are reported at GenBank accession numbers D16248.1 and D2823.1. Also, Finer et al. have discussed analysis of a soybean ubiquitin promoter, but did not provide a sequence (Finer et al., 2006). Thus there remains a need for the identification of structure and function of promoters and terminators, and a high expressing regulatory region would be especially desirable.

All references cited herein are incorporated herein by reference.

SUMMARY OF THE INVENTION

*Glycine max* polyubiquitin gene regulatory regions has been identified, and function as a promoter and terminator demonstrated. The invention is further directed to sequences which hybridize to same under highly stringent circumstances and functional fragments. In an embodiment, the regulatory element is used to regulate high level, constitutive expression of linked nucleotide sequences. A terminator region is used to further regulate expression of linked sequences.

DESCRIPTION OF THE DRAWINGS

FIG. 1A shows the promoter sequence of the invention with exogenous sequences including EcoRI, SbfI, ApaI and SacI restriction sites and the Kozak translation initiation consensus sequence (SEQ ID NO: 1). FIG. 1B shows the 911 base pair promoter sequence (SEQ ID NO: 2).

FIG. 2A shows the terminator sequence of the invention with additional exogenous sequence including XbaI, SbfI and XhoI restriction sites (SEQ ID NO: 3). FIG. 2B shows the 322 base pair terminator sequence (SEQ ID NO: 4).

DESCRIPTION OF THE PREFERRED EMBODIMENTS

Nucleotide sequences are described herein that regulate transcription with high constitutive expression in plant cells. These novel nucleotide sequences are those natively associated with the ubiquitin gene of *Glycine max*. The promoter element is the 911 base pair sequence shown in FIG. 1B (SEQ ID NO: 2). It includes the sequences up to but not including the translation start site, ATG. The terminator element is the 322 base pair sequence shown in FIG. 2B (SEQ ID NO: 4). The construction of this promoter provides a general method for the discovery of novel sequences with utility as promoters. The present invention is also directed to DNA molecules including said promoter, such as a DNA construct comprising the promoter operably linked to one or more genes or antisense DNA. The invention is further directed to transformed plant tissue including the DNA molecule and to transformed plants and seeds thereof. The promoter is useful for driving nucleotide sequences, for example, a gene or antisense expression for the purpose of imparting agronomically useful traits such as, but not limited to, increase in yield, disease resistance, insect resistance, herbicide tolerance, drought tolerance and salt tolerance in plants. Nucleotide sequences are described herein that regulate transcription with high constitutive expression in plant cells.

A recombinant host may be any prokaryotic or eukaryotic cell that contains either a cloning vector or an expression vector. This term also includes those prokaryotic or eukaryotic cells that have been genetically engineered to contain the cloned gene(s) in the chromosome or genome of the host cell. The promoter is, in an embodiment, particularly useful for the expression of nucleotide sequences in plants. It can be used in any plant species, including a dicotyledonous plant, such as, by way of example but not limitation, tobacco, tomato, potato, soybean, cotton, canola, sunflower or alfalfa. Alternatively, the plant may be a monocotyledonous plant, by way of example but not limitation, maize, wheat, rye, rice, oat, barley, turfgrass, sorghum, millet or sugarcane.

The nucleotide sequences of the invention can be used to isolate corresponding sequences from other organisms, particularly other plants, or to synthesize synthetic sequences. In this manner, methods such as polymerase chain reaction (PCR), hybridization, synthetic gene construction and the like can be used to identify or generate such sequences based on their sequence homology to the sequences set forth herein. Sequences identified, isolated or constructed based on their sequence identity to the whole of or any portion of the promoter sequences set forth is encompassed by the present invention. Synthesis of sequences suitably employed in the present invention can be effected by means of mutually priming long oligonucleotides. See for example, Wosnick et al. (1987). In a PCR approach, oligonucleotide primers can be designed for use in PCR reactions to amplify corresponding DNA sequences from cDNA or genomic DNA extracted from any plant of interest. Methods for designing PCR primers and PCR cloning are generally known in the art and are disclosed (Sambrook et al., 1989; Innis et al., 1990; Innis et al., 1995; Innis et al., 1999). Moreover, current techniques which employ the PCR reaction permit the synthesis of genes as large as 1.8 kilobases in length. See Adang et al. (1993) and Bambot et al. (1993). Known methods of PCR include, but are not limited to, methods using paired primers, nested primers, degenerate primers, gene-specific primers, vector-specific primers, partially-mismatched primers, and the like. In addition, genes can readily be synthesized by conventional automated techniques.

In hybridization techniques, all or part of a known nucleotide sequence is used as a probe that selectively hybridizes to other corresponding nucleotide sequences present in a population of cloned genomic DNA fragments or cDNA fragments (i.e., genomic or cDNA libraries) from a chosen organism. The hybridization probes may be genomic DNA fragments, cDNA fragments, RNA fragments, or other oligonucleotides, and may be labeled with a detectable group such as $^{32}$P, or any other detectable marker. Thus, for example, probes for hybridization can be made by labeling synthetic oligonucleotides based on the DNA sequences of the invention. Methods for preparation of probes for hybridization and for construction of cDNA and genomic libraries are generally known in the art and are disclosed (Sambrook et al., 1989).

For example, the promoter sequence disclosed herein, or one or more portions thereof, may be used as a probe capable of specifically hybridizing to corresponding sequences. To achieve specific hybridization under a variety of conditions, such probes include sequences that are unique among the sequences to be screened and are preferably at least about 10 nucleotides in length, and most preferably at least about 20 nucleotides in length. Such sequences may alternatively be used to amplify corresponding sequences from a chosen plant by PCR. This technique may be used to isolate sequences from a desired plant or as a diagnostic assay to determine the presence of sequences in a plant. Hybridization techniques include hybridization screening of DNA libraries plated as either plaques or colonies (Sambrook et al., 1989).

Hybridization of such sequences may be carried out under stringent conditions. By "stringent conditions" or "stringent hybridization conditions" is intended conditions under which a probe will hybridize to its target sequence to a detectably greater degree than to other sequences (e.g., at least 2-fold over background). Stringent conditions are sequence-dependent and will be different in different circumstances. By controlling the stringency of the hybridization and/or washing conditions, target sequences that are 100% complementary to the probe can be identified (homologous probing). Alternatively, stringency conditions can be adjusted to allow some mismatching in sequences so that lower degrees of similarity are detected (heterologous probing). Generally, a probe is less than about 1000 nucleotides in length, preferably less than 500 nucleotides in length.

Typically, stringent conditions will be those in which the salt concentration is less than about 1.5 M Na$^+$ ion, typically about 0.01 to 1.0 M Na$^+$ ion concentration (or other salts) at pH 7.0 to 8.3 and the temperature is at least about 30° C. for short probes (e.g., 10 to 50 nucleotides) and at least about 60° C. for long probes (e.g., greater than 50 nucleotides). Stringent conditions may also be achieved with the addition of destabilizing agents such as formamide. Exemplary low stringency conditions include hybridization with a buffer solution of 30 to 35% formamide, 1 M NaCl, 1% SDS (sodium dodecyl sulfate) at 37° C., and a wash in lx to 2×SSC (20×SSC=3.0 M NaCl/0.3 M trisodium citrate) at 50 to 55° C. Exemplary moderate stringency conditions include hybridization in 40 to 45% formamide, 1.0 M NaCl, 1% SDS at 37° C., and a wash in 0.5× to 1×SSC at 55 to 60° C. Exemplary high stringency conditions include hybridization in 50% formamide, 1.0 M NaCl, 0.1% SDS at 37° C., and a wash in 0.1×SSC at 60 to 65° C.

In general, sequences that correspond to the nucleotide sequences of the present invention and hybridize to the nucleotide sequence disclosed herein will be at least 50% homologous, 70% homologous, and even 85%, 86%, 87%, 88%, 89%, 90%, 91%, 92%, 93%, 94%, 95%, 96%, 97%, 98%, 99% homologous or more with the disclosed sequence. That is, the sequence similarity between probe and target may range, sharing at least about 50%, about 70%, and even about 85% or more sequence similarity.

Specificity is also the function of post-hybridization washes, the critical factors being the ionic strength and temperature of the final wash solution. For DNA-DNA hybrids, the $T_m$ can be approximated from the equation $T_m$=81.5° C.+16.6 (log M)+0.41(% GC)−0.61(% form.)−500/L, where M is the molarity of monovalent cations, % GC is the percentage of guanosine and cytosine nucleotides in the DNA, % form. is the percentage of formamide in the hybridization solution, and L is the length of the hybrid in base pairs (Meinkoth and Wahl, 1984). The $T_m$ is the temperature (under defined ionic strength and pH) at which 50% of a complementary target sequence hybridizes to a perfectly matched probe. $T_m$ is reduced by about 1° C. for each 1% of mismatching; thus, $T_m$, hybridization, and/or wash conditions can be adjusted for sequences of the desired identity to hybridize. For example, if sequences with 90% identity are sought, the $T_m$ can be decreased 10° C. Generally, stringent conditions are selected to be about 5° C. lower than the thermal melting point ($T_m$) for the specific sequence and its complement at a defined ionic strength and pH. However, severely stringent conditions can utilize a hybridization and/or wash at 1, 2, 3, or 4° C. lower than the thermal melting point ($T_m$); moderately stringent conditions can utilize a hybridization and/or wash at 6, 7, 8, 9, or 10° C. lower than the thermal melting point ($T_m$); low stringency conditions can utilize a hybridization and/or wash at 11 to 20° C. lower than the thermal melting point ($T_m$). Using the equation, hybridization and wash compositions, and desired $T_m$, those of ordinary skill will understand that variations in the stringency of hybridization and/or wash solutions are inherently described. If the desired degree of mismatching results in a $T_m$ of less than 45° C. (aqueous solution) or 32° C. (formamide solution), it is preferred to increase the SSC concentration so that a higher temperature can be used. An extensive guide to the hybridization of nucleic acids is found (1997) Ausubel et al, *Short Protocols in Molecular Biology*, page 2-40, Third Edit. (1997) and Sambrook et al. (1989).

Thus, isolated sequences that have regulatory element activity and which hybridize under stringent conditions to the promoter sequences disclosed herein, or to fragments thereof, are encompassed by the present invention.

The following terms are used to describe the sequence relationships between two or more nucleic acids or polynucleotides: (a) "reference sequence", (b) "comparison window", (c) "sequence identity" and (d) "percentage of sequence identity."

(a) As used herein, "reference sequence" is a defined sequence used as a basis for sequence comparison. A reference sequence may be a subset or the entirety of a specified sequence; for example, as a segment of a full-length promoter sequence, or the complete promoter sequence.

(b) As used herein, "comparison window" makes reference to a contiguous and specified segment of a polynucleotide sequence, wherein the polynucleotide sequence in the comparison window may comprise additions or deletions (i.e., gaps) compared to the reference sequence (which does not comprise additions or deletions) for optimal alignment of the two sequences. Generally, the comparison window is at least 20 contiguous nucleotides in length, and optionally can be 30, 40, 50, 100, or longer. Those of skill in the art understand that to accurately reflect the similarity to a reference sequence due to inclusion of gaps in the polynucleotide sequence a gap penalty is typically introduced and is subtracted from the number of matches.

Methods of alignment of sequences for comparison are well known in the art. Thus, the determination of percent identity between any two sequences can be accomplished using a mathematical algorithm. Preferred, non-limiting examples of such mathematical algorithms are the algorithm of Myers and Miller (1988), the local homology algorithm of Smith and Waterman (1981), the homology alignment algorithm of Needleman and Wunsch (1970), the search-for-similarity-method of Pearson and Lipman (1988) and the algorithm of Karlin and Altschul (1990), modified as in Karlin and Altschul (1993).

Computer implementations of these mathematical algorithms can be utilized for comparison of sequences to determine sequence identity. Such implementations include, but are not limited to: CLUSTAL in the PC/Gene program (available from Intelligenetics, Mountain View, Calif., USA); the ALIGN program (Version 2.0) and GAP, BESTFIT, BLAST, FASTA, and TFASTA in the Wisconsin Genetics Software Package, Version 8 (available from Genetics Computer Group (GCG), 575 Science Drive, Madison, Wis., USA). Alignments using these programs can be performed using the default parameters. The CLUSTAL program is well described by Higgins and Sharp (1988), Higgins and Sharp (1989), Corpet (1988), Huang et al. (1992) and Pearson (1994). The ALIGN program is based on the algorithm of Myers and Miller (1988). The BLAST programs of Altschul et al. (1990) are based on the algorithm of Karlin and Altschul (1990). To obtain gapped alignments for comparison purposes, Gapped BLAST (in BLAST 2.0) can be utilized as described in Altschul et al. (1997). Alternatively, PSI-BLAST (in BLAST 2.0) can be used to perform an iterated search that detects distant relationships between molecules, see Altschul et al. (1997). When utilizing BLAST, Gapped BLAST or PSI-BLAST, the default parameters of the respective programs (e.g. BLASTN for nucleotide sequences, BLASTX for proteins) can be used, see the World Wide Web site ncbi.nlm.nih.gov. Alignment may also be performed manually by inspection.

For purposes of the present invention, comparison of nucleotide sequences for determination of percent sequence identity to the promoter sequences disclosed herein is preferably made using the BlastN program (version 1.4.7 or later) with its default parameters or any equivalent program. By "equivalent program" is intended any sequence comparison program that, for any two sequences in question, generates an identical or similar alignment of nucleotide matches and percent sequence identity when compared to the corresponding alignment generated by the preferred program.

(c) As used herein, "sequence identity" or "identity" in the context of two nucleic acid sequences makes reference to the residues in the two sequences that are the same when aligned for maximum correspondence over a specified comparison window.

(d) As used herein, "percentage of sequence identity" means the value determined by comparing two optimally aligned sequences over a comparison window, wherein the portion of the polynucleotide sequence in the comparison window may comprise additions or deletions (i.e., gaps) as compared to the reference sequence (which does not comprise additions or deletions) for optimal alignment of the two sequences. The percentage is calculated by determining the number of positions at which the identical nucleic acid base occurs in both sequences to yield the number of matched positions, dividing the number of matched positions by the total number of positions in the window of comparison, and multiplying the result by 100 to yield the percentage of sequence identity.

Identity to the sequence of the present invention would mean a polynucleotide sequence having at least 65% sequence identity, more preferably at least 70% sequence identity, more preferably at least 75% sequence identity, more preferably at least 80% identity, more preferably at least 85% 86%, 87%, 88%, 89%, 90%, 91%, 92%, 93%, 94%, 95%, 96%, 97%, 98%, 99% sequence identity.

In accordance with one embodiment, a novel promoter is constructed by the following steps. The sequence of a known or newly discovered promoter is compared with known nucleic acid sequences, such as sequences in genomic databases. In one embodiment, this comparison is made in the GenBank database using a program such as FASTA (Genetics Computer Group, Madison, Wis.). Additional suitable databases and comparison programs are known to a person of skill in the art. Segments of sequence similar to the query sequence, i.e., the known or newly discovered promoter, are identified and selected. Segments are considered similar if they have between 60% and 100% sequence identity over the segment being examined. These segments can be 20-100 bases in length, although smaller or longer segments can also be selected. The selected sequences are aligned in linear order according to the sequence of the promoter being modified. The resultant promoter is a hybrid promoter comprised of sequences similar to but different from the original promoter. The short segments that make up the synthetic hybrid promoter may be parts of promoters or regulatory regions from other genes. The synthetic hybrid promoter is then constructed and empirically tested in a test expression system to determine its quantitative and qualitative characteristics. If the synthetic hybrid promoter has maintained or improved activity, it may be used directly. If the synthetic hybrid promoter has a lower activity, the sequence of the synthetic hybrid promoter is further modified by replacing some of the bases to generate a new hybrid promoter. The new hybrid promoter is again constructed and tested to determine if it has the desired maintained or improved activity. This procedure can be performed as often as necessary to derive the final hybrid promoter having the desired activity.

The invention is further to "functional variants" of the regulatory sequence disclosed. Functional variants include, for example, regulatory sequences of the invention having one or more nucleotide substitutions, deletions or insertions and wherein the variant retains promoter activity, particularly the ability to drive expression preferentially to the embryo of a plant. Functional variants can be created by any of a number of methods available to one skilled in the art, such as by site-directed mutagenesis, induced mutation, identified as allelic variants, cleaving through use of restriction enzymes, or the like. Activity can likewise be measured by any variety of techniques, including measurement of reporter activity as is described at U.S. Pat. No. 6,844,484, Northern blot analysis, or similar techniques. The '484 patent describes the identification of functional variants of different promoters.

The invention further encompasses a "functional fragment," that is, a regulatory sequence fragment formed by one or more deletions from a larger regulatory element. For example, the 5' portion of a promoter up to the TATA box near the transcription start site can be deleted without abolishing promoter activity, as described by Opsahl-Sorteberg, H-G. et al., 2004. Such fragments should retain promoter activity, particularly the ability to drive expression of operably linked nucleotide sequences. Activity can be measured by Northern blot analysis, reporter activity measurements when using transcriptional fusions, and the like. See, for example, Sambrook et al. (1989). Functional fragments can be obtained by use of restriction enzymes to cleave the naturally occurring regulatory element nucleotide sequences disclosed herein; by synthesizing a nucleotide sequence from the naturally occurring DNA sequence; or can be obtained through the use of PCR technology See particularly, Mullis et al. (1987) and Erlich, ed. (1989).

For example, a routine way to remove part of a DNA sequence is to use an exonuclease in combination with DNA amplification to produce unidirectional nested deletions of double stranded DNA clones. A commercial kit for this purpose is sold under the trade name Exo-Size™ (New England Biolabs, Beverly, Mass.). Briefly, this procedure entails incubating exonuclease III with DNA to progressively remove nucleotides in the 3' to 5' direction at 5' overhangs, blunt ends or nicks in the DNA template. However, exonuclease III is unable to remove nucleotides at 3',4-base overhangs. Timed digests of a clone with this enzyme produces unidirectional nested deletions.

By "promoter" is meant a regulatory element of DNA capable of regulating the transcription of a sequence linked thereto. It usually comprises a TATA box capable of directing RNA polymerase II to initiate RNA synthesis at the appropriate transcription initiation site for a particular coding sequence. The promoter is the minimal sequence sufficient to direct transcription in a desired manner. The term "regulatory element" is also used to refer to the sequence capable of "regulatory element activity," that is, initiating transcription in a desired manner. Therefore the invention is directed to the regulatory element described herein including those sequences which hybridize to same and have identity to same, as indicated, and fragments and variants of same which have regulatory activity.

The promoter of the invention may also be used in conjunction with another promoter. In one embodiment, the plant selection marker and the nucleotide sequence of interest can be both functionally linked to the same promoter. In another embodiment, the plant selection marker and the nucleotide sequence of interest can be functionally linked to different promoters. In yet third and fourth embodiments, the expression vector can contain two or more nucleotide sequences of interest that can be linked to the same promoter or different promoters. For example, the promoter described here can be used to drive the gene of interest and the selectable marker, or a different promoter used for one or the other. These other promoter elements can be those that are constitutive or sufficient to render promoter-dependent gene expression controllable as being cell-type specific, tissue-specific or time or developmental stage specific, or being inducible by external signals or agents. Such elements may be located in the 5' or 3' regions of the gene. Although the additional promoter may be the endogenous promoter of a structural gene of interest, the promoter can also be a foreign regulatory sequence. Promoter elements employed to control expression of product proteins and the selection gene can be any plant-compatible promoters. These can be plant gene promoters, such as, for example, a ubiquitin promoter (European patent application no. 0 342 926); the promoter for the small subunit of ribulose-1,5-bisphosphate carboxylase (ssRUBISCO) (Coruzzi et al., 1984; Broglie et al., 1984); or promoters from the tumor-inducing plasmids from *Agrobacterium tumefaciens*, such as the nopaline synthase, octopine synthase and mannopine synthase promoters (Velten and Schell, 1985) that have plant activity; or viral promoters such as the cauliflower mosaic virus (CaMV) 19S and 35S promoters (Guilley et al., 1982; Odell et al., 1985), the figwort mosaic virus FLt promoter (Maiti et al., 1997) or the coat protein promoter of TMV (Grdzelishvili et al., 2000).

The range of available plant compatible promoters includes tissue specific and inducible promoters. An inducible regulatory element is one that is capable of directly or indirectly activating transcription of one or more DNA sequences or genes in response to an inducer. In the absence of an inducer the DNA sequences or genes will not be transcribed. Typically the protein factor that binds specifically to an inducible regulatory element to activate transcription is present in an inactive form which is then directly or indirectly converted to the active form by the inducer. The inducer can be a chemical agent such as a protein, metabolite, growth regulator, herbicide or phenolic compound or a physiological stress imposed directly by heat, cold, salt, or toxic elements or indirectly through the actin of a pathogen or disease agent such as a virus. A plant cell containing an inducible regulatory element may be exposed to an inducer by externally applying the inducer to the cell or plant such as by spraying, watering, heating or similar methods. Any inducible promoter can be used in the instant invention. See Ward et al. (1993). Exemplary inducible promoters include ecdysone receptor promoters, U.S. Pat. No. 6,504,082; promoters from the ACE1 system which responds to copper (Mett et al. (1993)); In2-1 and In2-2 gene from maize which respond to benzenesulfonamide herbicide safeners (U.S. Pat. No. 5,364,780); the maize GST promoter, which is activated by hydrophobic electrophilic compounds that are used as pre-emergent herbicides; and the tobacco PR-1a promoter, which is activated by salicylic acid. Other chemical-regulated promoters of interest include steroid-responsive promoters (see, for example, the glucocorticoid-inducible promoter in Schena et al. (1991) and McNellis et al. (1998)) and tetracycline-inducible and tetracycline-repressible promoters (see, for example, Gatz et al. (1991), and U.S. Pat. Nos. 5,814,618 and 5,789,156). Alternatively, plant promoters such as heat shock promoters for example soybean hsp 17.5-E (Gurley et al., 1986); or ethanol-inducible promoters (Caddick et al., 1998) may be used. See International Patent Application No. WO 91/19806 for a review of illustrative plant promoters suitably employed in the present invention.

Tissue-preferred promoters can be utilized to target enhanced transcription and/or expression within a particular plant tissue. Promoters may express in the tissue of interest, along with expression in other plant tissue, may express strongly in the tissue of interest and to a much lesser degree than other tissue, or may express highly preferably in the tissue of interest. Tissue-preferred promoters include, for example, those described in Yamamoto et al. (1997); Kawamata et al. (1997); Hansen et al. (1997); Russell et al. (1997); Rinehart et al. (1996); Van Camp et al. (1996); Canevascini et al. (1996); Yamamoto et al. (1994); Lam (1994); Orozco et al. (1993); and Matsuoka et al. (1993).

A promoter can additionally comprise other recognition sequences generally positioned upstream or 5' to the TATA box, referred to as upstream promoter elements, which influence the transcription initiation rate. Using the promoter sequences disclosed here, it is possible to isolate and identify further regulatory elements in the 5' region upstream from the particular promoter region identified. Thus the promoter region disclosed is generally further defined by comprising upstream regulatory elements such as those responsible for high level and temporal expression of the coding sequence, enhancers and the like. In the same manner, the promoter elements which enable low to high level expression can be identified, isolated, and used with other core promoters to confirm embryo-preferred expression. By core promoter is meant the sequence sometimes referred to as the TATA box (or similar sequence) which is common to promoters in most genes encoding proteins. Thus the upstream promoter of the ubiquitin promoter can optionally be used in conjunction with its own or core promoters from other sources.

The promoter of the invention may be combined with any number of other components to be introduced into the plant, including combined with a nucleotide sequence of interest to be expressed in the plant. The "nucleotide sequence of interest" refers to a nucleotide sequence that encodes for a desired polypeptide or protein but also may refer to nucleotide sequences that do not constitute an entire gene, and which do not necessarily encode a polypeptide or protein. For example, when used in a homologous recombination process, the promoter may be placed in a construct with a sequence that targets an area of the chromosome in the plant but may not encode a protein. Use of antisense versions of a nucleic acid sequence is another example where use of a sequence may not result in an encoded protein. If desired, the nucleotide sequence of interest can be optimized for plant translation by optimizing the codons used for plants and the sequence around the translational start site for plants. Sequences resulting in potential mRNA instability can also be avoided.

In general, the methods available for construction of recombinant genes, optionally comprising various modifications for improved expression, can differ in detail. However, conventionally employed methods include PCR amplification, or the designing and synthesis of overlapping, complementary synthetic oligonucleotides, which are annealed and ligated together to yield a gene with convenient restriction sites for cloning, or subcloning from another already cloned source, or cloning from a library. The methods involved are standard methods for a molecular biologist (Sambrook et al., 1989). An expression vector is a DNA molecule comprising a gene or antisense DNA that is expressed in a host cell. Typically, gene expression is placed under the control of certain regulatory elements, including constitutive or inducible promoters, tissue-specific regulatory elements, and enhancers.

One skilled in the art readily appreciates that the promoter can be used with any of a variety of nucleotide sequences comprising the nucleotide sequence of interest to be expressed in plants. In referring to an operably linked nucleotide sequence is intended a functional linkage between a promoter and another sequence where the promoter initiates and mediates transcription of the nucleotide sequence. For example, the nucleotide sequence of interest may encode a protein that is useful for industrial or pharmaceutical purposes or the like, or to impact the plant itself, such as through expression of a protein that provides disease resistance, insect resistance, herbicide resistance, or impacts agronomic traits as well as grain quality traits. DNA sequences native to plants as well as non-native DNA sequences can be transformed into plants and used to modulate levels of native or non-native proteins. One or more of such sequences and/or expression cassettes may be transformed into a plant cell (in referring to a plant cell, it is intended to include cells without plant membranes, such as protoplasts).

Such nucleotide sequences include, but are not limited to, those examples provided below:

1. Genes that Confer Resistance to Pests or Disease (A) Plant Disease Resistance Genes. Plant defenses are often activated by specific interaction between the product of a disease resistance gene (R) in the plant and the product of a corresponding avirulence (Avr) gene in the pathogen. A plant variety can be transformed with cloned resistance gene to engineer plants that are resistant to specific pathogen strains. Examples of such genes include, the tomato Cf-9 gene for resistance to *Cladosporium falvum* (Jones et al., 1994), tomato Pto gene, which encodes a protein kinase, for resistance to *Pseudomonas syringae* pv. tomato (Martin et al., 1993), and *Arabidopsis* RSSP2 gene for resistance to *Pseudomonas syringae* (Mindrinos et al., 1994).

(B). A *Bacillus thuringiensis* protein, a derivative thereof or a synthetic polypeptide modeled thereon, such as, a nucleotide sequence of a Bt δ-endotoxin gene (Geiser et al., 1986). Moreover, DNA molecules encoding δ-endotoxin genes can be purchased from American Type Culture Collection (Rockville, Md.), under ATCC accession numbers. 40098, 67136, 31995 and 31998.

(C) A lectin, such as, nucleotide sequences of several *Clivia miniata* mannose-binding lectin genes (Van Damme et al., 1994).

(D) A vitamin binding protein, such as avidin and avidin homologs which are useful as larvicides against insect pests. See U.S. Pat. No. 5,659,026.

(E) An enzyme inhibitor, e.g., a protease inhibitor or an amylase inhibitor. Examples of such genes include, a rice cysteine proteinase inhibitor (Abe et al., 1987), a tobacco proteinase inhibitor I (Huub et al., 1993), and an α-amylase inhibitor Sumitani et al., 1993).

(F) An insect-specific hormone or pheromone such as an ecdysteroid and juvenile hormone a variant thereof, a mimetic based thereon, or an antagonist or agonist thereof, such as, baculovirus expression of cloned juvenile hormone esterase, an inactivator of juvenile hormone (Hammock et al., 1990).

(G) An insect-specific peptide or neuropeptide which, upon expression, disrupts the physiology of the affected pest. Examples of such genes include, an insect diuretic hormone receptor (Regan, 1994), an allostatin identified in *Diploptera punctata* (Pratt, 1989), insect-specific, paralytic neurotoxins (U.S. Pat. No. 5,266,361).

(H) An insect-specific venom produced in nature by a snake, a wasp, etc., such as, a scorpion insectotoxic peptide (Pang, 1992).

(I) An enzyme responsible for a hyperaccumulation of monoterpene, a sesquiterpene, a steroid, hydroxamic acid, a phenylpropanoid derivative or another non-protein molecule with insecticidal activity.

(J) An enzyme involved in the modification, including the post-translational modification, of a biologically active molecule; for example, glycolytic enzyme, a proteolytic enzyme, a lipolytic enzyme, a nuclease, a cyclase, a transaminase, an esterase, a hydrolase, a phosphatase, a kinase, a phosphorylase, a polymerase, an elastase, a chitinase and a glucanase, whether natural or synthetic. Examples of such genes include, a callas gene (PCT published application WO93/02197), chitinase-encoding sequences (which can be obtained, for example, from the ATCC under accession numbers 3999637 and 67152), tobacco hookworm chitinase (Kramer et al., 1993) and parsley ubi4-2 polyubiquitin gene (Kawalleck et al., 1993).

(K) A molecule that stimulates signal transduction. Examples of such molecules include, nucleotide sequences for mung bean calmodulin cDNA clones (Botella et al., 1994) and a nucleotide sequence of a maize calmodulin cDNA clone (Griess et al., 1994).

(L) A hydrophobic moment peptide. See U.S. Pat. Nos. 5,659,026 and 5,607,914, the latter teaches synthetic antimicrobial peptides that confer disease resistance.

(M) A membrane permease, a channel former or a channel blocker, such as, a cecropin-β lytic peptide analog (Jaynes et al., 1993) which renders transgenic tobacco plants resistant to *Pseudomonas solanacearum*.

(N) A viral-invasive protein or a complex toxin derived there from. For example, the accumulation of viral coat proteins in transformed plant cells imparts resistance to viral infection and/or disease development effected by the virus from which the coat protein gene is derived, as well as by related viruses. Coat protein-mediated resistance has been conferred upon transformed plants against alfalfa mosaic virus, cucumber mosaic virus, tobacco streak virus, potato virus X, potato virus Y, tobacco etch virus, tobacco rattle virus and tobacco mosaic virus. See, for example, Beachy et al. (1990).

(O) An insect-specific antibody or an immunotoxin derived there from. Thus, an antibody targeted to a critical metabolic function in the insect gut would inactive an affected enzyme, killing the insect. For example, Taylor et al. (1994) shows enzymatic inactivation in transgenic tobacco via production of single-chain antibody fragments.

(P) A virus-specific antibody. See, for example, Tavladoraki et al. (1993), which shows that transgenic plants expressing recombinant antibody genes are protected from virus attack.

(Q) A developmental-arrestive protein produced in nature by a pathogen or a parasite. Thus, fungal endo α-1,4-D polygalacturonases facilitate fungal colonization and plant nutrient release by solubilizing plant cell wall homo-α-1,4-D-galacturonase (Lamb et al., 1992). The cloning and characterization of a gene which encodes a bean endopolygalacturonase-inhibiting protein is described by Toubart et al. (1992).

(R) A developmental-arrestive protein produced in nature by a plant, such as, the barley ribosome-inactivating gene has an increased resistance to fungal disease (Longemann et al., 1992).

2. Genes that Confer Resistance to a Herbicide (A) A herbicide that inhibits the growing point or meristem, such as an imidazalinone or a sulfonylurea. Exemplary genes in this category code for mutant ALS (Lee et al., 1988) and AHAS enzyme (Miki et al., 1990).

(B) Glyphosate (resistance imparted by mutant EPSP synthase and aroA genes, respectively) and other phosphono compounds such as glufosinate (PAT and bar genes), and pyridinoxy or phenoxy proprionic acids and cyclohexones (ACCase inhibitor encoding genes). See, for example, U.S. Pat. No. 4,940,835, which discloses the nucleotide sequence of a form of EPSP which can confer glyphosate resistance. A DNA molecule encoding a mutant aroA gene can be obtained under ATCC accession number 39256, and the nucleotide sequence of the mutant gene is disclosed in U.S. Pat. No. 4,769,061. European patent application No. 0 333 033 and U.S. Pat. No. 4,975,374 disclose nucleotide sequences of glutamine synthetase genes which confer resistance to herbicides such as L-phosphinothricin. The nucleotide sequence of a phosphinothricinacetyl-transferase gene is provided in European application No. 0 242 246. De Greef et al. (1989) describes the production of transgenic plants that express chimeric bar genes coding for phosphinothricin acetyl transferase activity. Exemplary of genes conferring resistance to phenoxy proprionic acids and cyclohaexones, such as sethoxydim and haloxyfop, are the Accl-S1, Accl-S2 and Accl-S3 genes described by Marshall et al. (1992).

(C) A herbicide that inhibits photosynthesis, such as a triazine (psbA and gs+ genes) and a benzonitrile (nitrilase gene). Przibilla et al. (1991) describes the use of plasmids encoding mutant psbA genes to transform *Chlamydomonas*. Nucleotide sequences for nitrilase genes are disclosed in U.S. Pat. No. 4,810,648, and DNA molecules containing these genes are available under ATCC accession numbers 53435, 67441 and 67442. Cloning and expression of DNA coding for a glutathione S-transferase is described by Hayes et al. (1992).

3. Genes that Confer or Contribute to a Value-Added Trait (A) Modified fatty acid metabolism, for example, by transforming maize or *Brassica* with an antisense gene or stearoyl-ACP desaturase to increase stearic acid content of the plant (Knultzon et al., 1992).

(B) Decreased phytate content (1) Introduction of a phytase-encoding gene would enhance breakdown of phytate, adding more free phosphate to the transformed plant, such as the *Aspergillus niger* phytase gene (Hartingsveldt et al., 1993).

(2) A gene could be introduced that reduces phytate content. In maize, this, for example, could be accomplished by cloning and then reintroducing DNA associated with the single allele which is responsible for maize mutants characterized by low levels of phytic acid (Raboy et al., 1990).

(C) Modified carbohydrate composition effected, for example, by transforming plants with a gene coding for an enzyme that alters the branching pattern of starch. Examples of such enzymes include, *Streptococcus* mucus fructosyl-transferase gene (Shiroza et al., 1988), *Bacillus subtilis* levan-sucrase gene (Steinmetz et al., 1985), *Bacillus licheniformis* α-amylase (Pen et al., 1992), tomato invertase genes (Elliot et al., 1993), barley amylase gene (Sogaard et al., 1993), and maize endosperm starch branching enzyme II (Fisher et al., 1993).

The nucleotide sequence of interest can also be a nucleotide sequence used to target an area of the plant genome through homologous recombination. The promoter may be placed in a construct with such sequence, which sequence will not necessarily encode a protein. The sequence recombines in the genome and the promoter may be placed at the desired site targeted by the sequences to regulate the desired endogenous nucleotide sequence.

Further, the promoter can be used to drive mRNA that can be used for a silencing system, such as antisense, and in that instance, no protein is produced. Nellen et al. (1993); Alexander et al. (1988). Means of increasing or inhibiting a protein are well known to one skilled in the art and, by way of example, may include, transgenic expression, antisense suppression, use of hairpin formations, co-suppression methods including but not limited to: RNA interference, gene activation or suppression using transcription factors and/or repressors, mutagenesis including transposon tagging, directed and site-specific mutagenesis, chromosome engineering and, homologous recombination. In the case of use with homologous recombination, no in vivo construct will be required. A few of the myriad of examples of such systems available include use of the Mu transposon, Chandler et al. (1994); RNA interference (U.S. Pat. No. 5,034,323); use of hairpins, Smith et al. (2000) and ribozymes (Steinecke et al. (1992); and zinc-finger targeted molecules, WO 01/52620. Clearly many options are available for impacting a targeted protein.

A terminator region may also be included in the vector. An embodiment of the invention is the terminator sequence of the soybean ubiquitin gene, SEQ ID NO: 4. In referring to a terminator sequence is meant a nucleotide sequence that signals the end of transcription. Convenient termination regions are available from the Ti-plasmid of *A. tumefaciens*, such as the octopine synthase (MacDonald et al., 1991) and nopaline synthase termination regions. Examples of various other terminators include the pin II terminator from the protease inhibitor II gene from potato (An et al., 1989). See also, Guerineau et al. (1991); Proudfoot (1991); Sanfacon et al. (1991); Mogen et al. (1990); Munroe et al. (1990); Ballas et al. (1989); and Joshi et al. (1987).

In one embodiment, the expression vector also contains a nucleotide sequence encoding a selectable or scoreable marker that is operably or functionally linked to a promoter that controls transcription initiation, which can be the promoter of the invention or another promoter. For a general description of plant expression vectors and reporter genes, see Gruber et al. (1993). For example, the selective gene is a glufosinate-resistance encoding DNA or phosphinothricin acetyl transferase (pat) or a maize optimized pat gene, or bar gene can be used under the control of the CaMV 35S or other promoter. Such pat genes confer resistance to the herbicide bialaphos (Gordon-Kamm et al., 1990; Wohllenben et al. 1988). Other examples, without intending to be limiting, are hygromycin phosphotransferase, EPSP synthase and dihydropteroate encoding genes. See Miki et al. (1993). Scorable or screenable markers may also be employed, where presence of the sequence produces a visual and/or measurable product. Examples include a β-glucuronidase, or uidA gene (GUS), which encodes an enzyme for which various chromogenic substrates are known (for example, U.S. Pat. Nos. 5,268,463 and 5,599,670)

The expression vector can optionally also contain a signal sequence located between the promoter and the gene of interest and/or after the gene of interest. A signal sequence is a nucleotide sequence, translated to give an amino acid sequence, which is used by a cell to direct the protein or polypeptide of interest to be placed in a particular place within or outside the eukaryotic cell. One example of a plant signal sequence is the barley α-amylase secretion signal (Rogers, 1985). Many signal sequences are known in the art. See, for example Becker et al. (1992), Fontes et al. (1991), Matsuoka and Nakamura (1991), Gould et al. (1989), Creissen et al. (1992), Kalderon et al. (1984) and Stiefel et al. (1990).

Leader sequences can be included to enhance translation. Various available leader sequences may be substituted or added. Translation leaders are known in the art and include, for example: picornavirus leaders, for example, EMCV leader (encephalomyocarditis 5' noncoding region) (Elroy-Stein et al. (1989); potyvirus leaders, for example, TEV leader (Tobacco Etch Virus) (Gallie et al. (1995)); human immunoglobulin heavy-chain binding protein (BiP) (Macejak et al. (1991)); untranslated leader from the coat protein mRNA of alfalfa mosaic virus (AMV RNA 4) (Jobling et al. (1987)); tobacco mosaic virus leader (TMV) (Gallie. (1987)); and maize chlorotic mottle virus leader (MCMV) (Lommel et al. (1991)). See also, Della-Cioppa et al. (1987). Other methods known to enhance translation can also be utilized, for example, introns, and the like. Obviously, many variations on the promoters, selectable markers, signal sequences, leader sequences, termination sequences, introns, enhancers and other components of the vector are available to one skilled in the art.

Where appropriate, the nucleotide sequence (s) may be optimized for increased expression in the transformed plant. That is, the genes can be synthesized using plant-preferred codons for improved expression. See, for example, Campbell and Gowri (1990) for a discussion of host-preferred codon usage. Methods are available in the art for synthesizing plant-preferred genes. See, for example, U.S. Pat. Nos. 5,380,831, 5,436,391, and Murray et al. (1989). Additional sequence modifications are known to enhance gene expression in a plant. These include elimination of sequences encoding spurious polyadenylation signals, exon-intron splice site signals, transposon-like repeats, and other such well-characterized sequences that may be deleterious to gene expression. The G-C content of the sequence may be adjusted to levels average for a given cellular host, as calculated by reference to known genes expressed in the host cell. When possible, the sequence is modified to avoid predicted hairpin secondary mRNA structures.

In preparing the nucleotide construct, the various nucleotide sequence fragments can be manipulated, so as to provide for the nucleotide sequences in the proper orientation and, as appropriate, in the proper reading frame. Toward this end, adapters or linkers can be employed to join the nucleotide sequence fragments or other manipulations may be involved to provide for convenient restriction sites, removal of superfluous nucleotide sequences, removal of restriction sites, or the like. For this purpose, in vitro mutagenesis, primer repair, restriction, annealing, resubstitutions, e.g., transitions and transversions, may be involved.

Methods for introducing expression vectors into plant tissue available to one skilled in the art are varied and will depend on the plant selected. Procedures for transforming a wide variety of plant species are well known and described throughout the literature. See, for example, Miki and McHugh (2004); Klein et al. (1992); and Weising et al. (1988). For example, the DNA construct may be introduced into the genomic DNA of the plant cell using techniques such as microprojectile-mediated delivery (Klein et al. 1992), electroporation (Fromm et al., 1985), polyethylene glycol (PEG) precipitation (Mathur and Koncz, 1998), direct gene transfer (WO 85/01856 and EP-A-275 069), in vitro protoplast transformation (U.S. Pat. No. 4,684,611), and microinjection of plant cell protoplasts or embryogenic callus (Crossway, 1985). *Agrobacterium* transformation methods of Ishida et al. (1996) and also described in U.S. Pat. No. 5,591,616 are yet another option. Co-cultivation of plant tissue with *Agrobacterium tumefaciens* is a variation, where the DNA constructs are placed into a binary vector system (Ishida et al., 1996). The virulence functions of the *Agrobacterium tumefaciens* host will direct the insertion of the construct into the plant cell DNA when the cell is infected by the bacteria. See, for example, Fraley et al. (1983). *Agrobacterium* is primarily used in dicots, but monocots including maize can be transformed by *Agrobacterium*. See, for example, U.S. Pat. No. 5,550,318. In one of many variations on the method, *Agrobacterium* infection of corn can be used with heat shocking of immature embryos (Wilson et al. U.S. Pat. No. 6,420,630) or with antibiotic selection of Type II callus (Wilson et al., U.S. Pat. No. 6,919,494).

Rice transformation is described by Hiei et al. (1994) and Lee et al. (1991). Standard methods for transformation of canola are described by Moloney et al. (1989). Corn transformation is described by Fromm et al. (1990) and Gordon-Kamm et al. (1990). Wheat can be transformed by techniques similar to those used for transforming corn or rice. Sorghum transformation is described by Casas et al. (1993) and barley transformation is described by Wan and Lemaux (1994). Soybean transformation is described in a number of publications, including U.S. Pat. No. 5,015,580.

In one preferred method, use of aerosol beam technology for introduction of nucleotide sequences into cells is employed. Aerosol beam technology employs the jet expansion of an inert gas as it passes from a region of higher gas pressure to a region of lower gas pressure through a small orifice. The expanding gas accelerates aerosol droplets containing the molecules to be introduced into a cell or tissue. Aerosol droplets produced are typically less than 0.1 micron in diameter at the point of impact with the target cells. DNA carried in aerosol droplets of this small size penetrates cells only because of the speeds attained by the aerosol droplets. Speeds achieved by the aerosol beam method of the invention are supersonic and can reach 2000 meters/second. In a preferred embodiment, the process includes (I) culturing a source of cells, (II) optionally, pretreating cells to yield tissue with increased capacity for uptake and integration by aerosol beam technology, (III) transforming said tissue with an exogenous nucleotide sequence by the aerosol beam method of the invention, (IV) optionally, identifying or selecting for transformed tissue, (V) optionally regenerating transgenic plants from the transformed cells or tissue, and (VI) optionally, producing progeny of said transgenic plants. This process is described in detail at Held et al., U.S. Pat. Nos. 6,809,232; 7,067,716; and 7,026,286 (these references, as all cited references, are incorporated herein by reference).

In accordance with the present invention, a transgenic plant can be produced that contains an introduced soybean ubiqutin promoter. It can be combined with any one of the components set forth above.

In a further embodiment, plant breeding can be used to introduce the nucleotide sequences into other plants once transformation has occurred. This can be accomplished by any means known in the art for breeding plants such as, for example, cross pollination of the transgenic plants that are described above with other plants, and selection for plants from subsequent generations which contain the nucleic acid and/or express the amino acid sequence or trait. The plant breeding methods used herein are well known to one skilled in the art. For a discussion of plant breeding techniques, see Poehlman and Sleper (1995). Many crop plants useful in this method are bred through techniques that take advantage of the plant's method of pollination. A plant is self-pollinating if pollen from one flower is transferred to the same or another flower of the same plant. A plant is cross-pollinating if the pollen comes from a flower on a different plant. For example, in *Brassica*, the plant is normally self-sterile and can only be cross-pollinated unless, through discovery of a mutant or through genetic intervention, self-compatibility is obtained. In self-pollinating species, such as rice, oats, wheat, barley, peas, beans, soybeans, tobacco and cotton, the male and female plants are anatomically juxtaposed. During natural pollination, the male reproductive organs of a given flower pollinate the female reproductive organs of the same flower. Maize plants (*Zea mays* L.) can be bred by both self-pollination and cross-pollination techniques. Maize has male flowers, located on the tassel, and female flowers, located on the ear, on the same plant. It can self or cross-pollinate.

Pollination can be by any means, including but not limited to hand, wind or insect pollination, or mechanical contact between the male fertile and male sterile plant. For production of hybrid seeds on a commercial scale in most plant species pollination by wind or by insects is preferred. Stricter control of the pollination process can be achieved by using a variety of methods to make one plant pool male sterile, and the other the male fertile pollen donor. This can be accomplished by hand detasslng, cytoplasmic male sterility, or control of male sterility through a variety of methods well known to the skilled breeder. Examples of more sophisticated male sterility systems include those described by Brar et al., U.S. Pat. Nos. 4,654,465 and 4,727,219 and Albertsen et al., U.S. Pat. Nos. 5,859,341 and 6,013,859.

Backcrossing methods may be used to introduce the gene into the plants. This technique has been used for decades to introduce traits into a plant. An example of a description of this and other plant breeding methodologies that are well known can be found in references such as Poehlman et al. (1995). In a typical backcross protocol, the original variety of interest (recurrent parent) is crossed to a second variety (nonrecurrent parent) that carries the single gene of interest to be transferred. The resulting progeny from this cross are then crossed again to the recurrent parent and the process is repeated until a plant is obtained wherein essentially all of the desired morphological and physiological characteristics of the recurrent parent are recovered in the converted plant, in addition to the single transferred gene from the nonrecurrent parent.

EXAMPLES

The following is presented as illustrative of an embodiment of the invention and does not limit the scope of the invention as otherwise set forth.

Example 1

Isolation of Soybean Ubiquitin Promoter and Terminator

Soybean genomic DNA was isolated using the DNeasy Plant Mini Kit (Qiagen, Valencia, Calif.) and used as a template for polymerase chain reaction (PCR) amplification with primers. Primers were designed as set forth below—based on the Xia et al., supra, sequence for soybean ubiquitin gene SOYSUBI3 (GenBank accession D28123.1)—and contained restriction enzyme sites corresponding to the restriction enzyme sites on the selected expression vector:

promoter forward primer gmup5 (39-mer):

```
      EcoRI SbfI
                                  (SEQ ID NO: 5)
gaattcctgcagggcccaatataacaacgacgtcgtaac
``` promoter reverse primer gmup3n (40-mer):

```
      SacI  zoK
                                  (SEQ ID NO: 6)
gagctcggcggcctgtcgagtcaacaatcacagataaatc
```

The restrictions sites are shown above along with the "Kozak" sequence, with the consensus sequence for translational initiation region indicated in italics (Kozak, M. (1987)). The PCR products were electrophoresed on a 0.8% agarose gel and the 911-bp amplicon was excised from the gel. The purified amplicon was ligated into the pGEM T-easy Vector System (Promega, Madison, Wis.) and the ligation mixture was introduced into competent E. coli DHa cells. Transformants were selected on Luria agar plates supplemented with ampicillin (100 µg/ml) and a recombinant clone containing the 911-bp promoter (named pGEM/gmubipro) was identified by EcoRI/SacI digestion of the plasmid DNAs prepared from selected putative recombinants.

The 911-base pair insert in pgmubipro was sequenced (at the DNA Facility, Iowa State University). The nucleotide sequence is shown in FIG. 1B (SEQ ID NO: 2). The sequence was compared using GAP analysis to the Xia et al. sequence and was found to share 96% identity to SOYSUBI3 sequence, Genbank D28123 and 90% identity to SOYSUBI1, GenBank D16248, a partial earlier reported sequence. A comparison with an *Arabidopsis* polyubiquitin3 promoter, showed about 38% identity (Bevan et al. Genbank AL163002) and comparison with the maize polyubiquitin promoter (Quail et al, U.S. Pat. No. 6,020,190) showed about 39% identity. The promoter appeared to be an intronless type promoter based upon NetGene2 predictions (Center for Biological Sequence Analysis, the Technical University of Denmark, DK-2800, Lyngby, Denmark.

The same procedure was used to isolate the terminator (gmubiter), using the following primers prepared based on Xia et al., GenBank sequence D28123:

terminator forward primer(41-mer):

```
      XhoI  SbfI
                                  (SEQ ID NO: 7)
ctcgagcctgcaggatgatcaccatccttcacacaactcatccc
``` terminator reverse primer(41-mer):

```
      XhoI  SbfI
                                  (SEQ ID NO: 8)
ctcgagcctgcagggaattcgaaggatgatcaccatccttc
```

The sequence identified is shown in FIG. 2B (SEQ ID NO: 4). A GAP analysis with SOYSUBI3, showed 100% identity, and 86-90% identity to SOYSUB1.

Example 2

Construction of Plasmids Used in Soybean Transformation

Plasmid pSTgmubipro-gus-nos was constructed as follows: The gmubipromoter was taken as a EcoRI/SacI fragment from the pGEM/gmubipro construct and was introduced into EcoRI/SacI digested pSLJ4k1 to generate p4k1-gmubipro-GUS-Nos. (Plasmid pSLJ4k1 had the GUS reporter gene under the control of the CaMV 35S promoter and the nopaline syntase-nos-terminator and was obtained from the Sainsbury Laboratory at the John Innes Center, England). Plasmid pSTBMuNos consisted of a MuA promoter, 0.25 kb nopaline syntase 3' end (nos) in a pUC18 backbone. The MuA promoter was removed from the plasmid pSTBMuNos by EcoRI and XbaI double digestion and was replaced by the EcoRI/XbaI fragment from p4k1-gmubipro-GUS-Nos which contained the gmubipro/GUS unit. This generated the pgmubipro-GUS-Nos construct. The Nos terminator in pgmubipro-GUS-Nos was removed as a XbaI/XhoI fragment and was replaced by a XbaI/XhoI fragment containing the gmubiter unit.

Example 3

Transformation of Cotledonary Explants of Soybean

Cotyledonary nodes were prepared from 5-7-day-old seedlings as described by Paz et al. The plasmids described above were introduced into cells of the explants by aerosol beam injection. To evaluate the transient expression potential of the newly constructed promoter/terminator, GUS activity staining was performed on the nodes 24 hours after the aerosol beam treatment.

The above plasmids were also introduced into embryogenic callus tissues (that were initiated from immature cotyledons) by the aerosol beam injection technology to obtain stable transgenic soybean plants.

The embryogenic soybean callus was transferred after a culture passage of about 28 to 30 days from stock culture medium according to U.S. Pat. No. 6,809,232 to the center of a target plate containing the same medium. Embryogenic soybean callus can survive being held in a vacuum for at least 10 minutes. After one to three days' growth on the target plate, the soybean embryogenic callus is exposed to an aerosol beam of the plasmid. After beaming, the tissue is spread out on a fresh plate (to minimize the risk of contamination) of the same medium. Whole plants were obtained from the transformed tissues according to U.S. Pat. No. 6,809,232.

Briefly, the treatment of target tissue with the aerosol beam apparatus was performed as follows: 1) place petri dish with tissue on the stage and close vacuum chamber; 2) start the vacuum pump; 3) start the syringe pump; 4) set the nebulizing gas pressure; 5) set the entrainment gas pressure, and by this time the correct vacuum in the chamber is reached; and 6) start the movement of the stage and let the system run for the time needed to complete the run. After the run is completed, shut down the stage, vacuum, syringe pump, nebulizing gas, entrainment gas, and remove target tissue from the chamber.

The aerosol was produced by a microflow nebulizer such as the HEN from J.E. Meinhard Associates Inc., or the MCN100 style M4 nebulizer from Cetac Technologies Inc. (Liu and Montaser, 1994; Tan, et al., 1992). The nebulizing gas was high purity compressed-helium which was regulated with an ACCU-TROL gas regulator—876X model RS-7-4 and filtered through an Arrow F300-02 IT filter. When HEN and the MCN100 microflow nebulizers were used, the nebulizing pressure was preferably 20-30 psi but worked within the range from about 10 psi to about 40 psi. The entrainment gas filled the entrainment tube and entrained the aerosol droplets in a straight line. Unfiltered, high purity compressed helium was used as the entrainment gas and was regulated by an Arrow R262 regulator to produce slight positive pressure as measured by a Gilmont model 65 mm gauge. The entrainment housing contained a nucleospot to reduce electrostatic charges and was maintained at a temperature of about 42° C. to about 55° C., and most preferably about 55° C. This reduced coalescing of the aerosol droplets and was controlled by two Omega CN9000 series temperature controllers. The sample flow rate to the nebulizer was controlled by a Harvard 11 infusion only syringe pump. The flow rate was 1 to 1200 μl/min using a sterile Becton Dickinson 1 cc plastic syringe with a 0.2 micron filter attached. The sample contained 10 mM Tris buffer (pH 7.0) or a carbohydrate molecule (for example 1 g/l sucrose) and the molecules to be delivered.

Example 4

Analysis of GUS Expression

Assays were performed to determine GUS activity resulting from expression of the uidA reporter gene (Jefferson et al., 1987). Representative tissue samples were collected and were incubated overnight at 37° C. with Jefferson's buffer containing 0.5 $mgml^{-1}$ X-gluc (Jefferson et al., 1987). Blue staining indicated GUS activity. Following the transformation GUS expression was assessed in the cotyledonary tissue. Strong GUS activity was detected in the transformed explants. Analysis using the 35S promoter/GUS reporter/OCS terminator construct and the soybean ubiquitin promoter/GUS reporter/soybean ubiquitin terminator construct revealed comparable expression level (comparable GUS staining) for the two constructs studied.

GUS activity was measured in the leaf, stem, and root tissues of $T_1$ soybean plants transformed with the soybean ubiquitin promoter/GUS reporter/soybean ubiquitin terminator construct. Tissues from two independent events were used in the GUS activity assays. Intense blue staining in all the tested tissues (from both events) was observed. The leaf, stem, and root tissues taken from a transgenic plant that did not contain the soybean ubiquitin promoter/GUS reporter/soybean ubiquitin terminator construct, on the other hand, did not stain blue in the GUS activity assays. These results demonstrate the ability of the soybean ubiquitin promoter to direct the expression of the β-glucuronidase enzyme in all the tissues.

As can be seen, the invention can be practiced with a number of variations known to one skilled in the art and achieves it objectives

REFERENCES

Abe et al. (1987) J. Biol. Chem. 262:16793

Adang et al. (1993), Plant Molec. Biol. 21:1131.

Altschul, S. F., Gish, W., Miller, W., Myers, E. W. and Lipman, D. J. (1990) Basic local alignment search tool. J. Mol. Biol. 215, 403-410.

Altschul, S. F., Madden, T. L., Schaffer, A. A., Zhang, J., Zhang, Z., Miller, W. and Lipman, D. J. (1997) Nucleic Acids Res. 25, 3389-3402.

Alexander et al. (1988) Gene 72:45-50

An, G., Mitra, A., Choi, H. K., Costa, M. A., An, K., Thornburg, R. W. and Ryan, C. A. (1989) Functional analysis of the 3' control region of the potato wound-inducible proteinase inhibitor II gene. Plant Cell 1, 115-122.

Ausubel et al, (1997) *Short Protocols in Molecular Biology*, page 2-40, Third Edit.

Ballas et al. (1989) Nucleic Acids Res. 17:7891-7903

Bambot et al. (1993). PCR Methods and Applications 2:266

Beachy et al. (1990) Ann. Rev. Phytopathol. 28:451 Becker, T. W., Templeman, T. S., Viret, J. F. and Bogorad, L. (1992) The cab-m7 gene: a light-inducible, mesophyll-specific gene of maize. Plant Mol. Biol. 20, 49-60.

Broglie, R., Coruzzi, G., Fraley, R. T., Rogers, S. G., Horsch, R. B., Niedermeyer, J. G., Fink, C. L. and Chua, N. H. (1984) Light-regulated expression of a pea ribulose-1,5-bisphosphate carboxylase small subunit gene in transformed plant cells. Science 224, 838-843.

Bustos, M. M., Guiltinan, M. J., Jordano, J., Begum, D., Kalkan, F. A. and Hall, T. C. (1989) Regulation of beta-glucuronidase expression in transgenic tobacco plants by an A/T-rich, cis-acting sequence found upstream of a French bean beta-phaseolin gene. Plant Cell 1, 839-853.

Caddick M. X., Greenland, A. J., Jepson, I., Krause, K. P., Qu, N., Riddell, K. V., Salter, M. G., Schuch, W., Sonnewald, U. and Tomsett, A. B. (1998) An ethanol inducible gene switch for plants used to manipulate carbon metabolism. Nat. Biotechnol. 16, 177-180.

Campbell and Gowri (1990) Plant Physiol. 92:1-11

Canevascini et al. (1996) Plant Physiol. 112(2): 513-524

Casas, A. M., Kononowicz, A. K., Zehr, U. B., Tomes, D. T., Axtell, J. D., Butler, L. G., Bressan, R. A. and Hasegawa P. M. (1993) Transgenic sorghum plants via microprojectile bombardment. Proc. Natl. Acad. Sci. USA 90, 11212-11216.

Chandler, (1994) *The Maize handbook* ch. 118 Springer-Verlag

Corpet, F. (1988) Multiple sequence alignment with hierarchical clustering. Nucleic Acids Res. 16, 10881-10890.

Coruzzi, G., Broglie, R., Edwards, C. and Chua, N. H. (1984) Tissue-specific and light-regulated expression of a pea nuclear gene encoding the small subunit of ribulose-1,5-bisphosphate carboxylase. EMBO J. 3, 1671-1679.

Creissen, G., Edwards, E. A., Enard, C., Wellburn, A. and Mullineaux, P. (1992) Molecular characterization of glutathione reductase cDNA from pea (*Pisum sativum* L.). Plant J. 2, 129-131.

Crossway, A. (1985) Mol. Gen. Genet. 202, 179-185.

De Greef et al. (1989) Bio/Technology 7:61.

Della-Cioppa et al. (1987) Plant Physiology 84:965-968.

Elliott et al. (1993) Plant Molec. Biol. 21:515

Elroy-Stein et al. (1989) Proc. Natl. Acad. Sci. USA 86:6126-6130.

Erlich, ed. (1989) *PCR Technology* (Stockton Press, New York).

Finer et al. "Characterization of soybean promoters through evaluation of GFP expression in transgenic soybean" The 11th Biennial Conference on the Molecular & Cellular Biology of the Soybean, Aug. 5-8, 2006, University of Nebraska, Lincoln, Nebr.

fisher et al. (1993) Plant Physiol. 102:1045.

Fontes, E. B., Shank, B. B., Wrobel, R. L., Moose, S. P., OBrian, G. R., Wurtzel, E. T. and Boston, R. S. (1991) Characterization of an immunoglobulin binding protein homolog in the maize floury-2 endosperm mutant. Plant Cell 3, 483-496.

Fraley, R. T., Rogers, S. G., Horsch, R. B., Sanders, P. R., Flick, J. S., Adams, S. P., Bittner, M. L., Brand, L. A., Fink, C. L., Fry, J. S., Galluppi, G. R., Goldberg, S. B., Hoffmann, N. L. and Woo, S. C. (1983) Expression of bacterial genes in plant cells. Proc. Natl. Acad. Sci. USA, 80, 4803-4807.

Fromm, M., Taylor, L. P. and Walbot, V. (1985) Expression of genes transferred into monocot and dicot plant cells by electroporation. Proc. Natl. Acad. Sci, USA 82, 5824-5828.

Fromm, M. E., Morrish, F., Armstrong, C., Williams, R., Thomas, J. and Klein, T. M. (1990) Inheritance and expression of chimeric genes in the progeny of transgenic maize plants. Biotechnology (N Y) 8, 833-839.

Gallie et al. (1987) The 5' leader sequence of tobacco mosaic virus RNA enhances the expression of foreign gene transcripts in vitro and in vivo. Nucleic Acids Res. 15(8):3257-73

Gallie et al. (1995) The tobacco etch viral 5' leader and poly(A) tail are functionally synergistic regulators of translation. Gene 165 (2):233-8.

Gatz et al. (1991) Mol. Gen. Genet. 227:229-237

Gordon-Kamm, W., Dilkes, B. P., Lowe, K., Hoerster, G., Sun, X., Ross, M., Church, L., Bunde, C., Farrell, J., Hill, P., Maddock, S., Snyder, J., Sykes, L., Li, Z., Woo, Y. M., Bidney, D. and Larkins, B. A. (1990) Transformation of maize cells and regeneration of fertile transgenic plants. Plant Cell 2, 603-618.

Gould, S. J., Keller, G. A., Hosken, N., Wilkinson, J. and Subramani, S. (1989) A conserved tripeptide sorts proteins to peroxisomes. J. Cell. Biol. 108, 1657-1664.

Grdzelishvili, V. Z., Chapman, S. N., Dawson, W. O. and Lewandowski, D. J. (2000) Mapping of the tobacco mosaic virus movement protein and coat protein subgenomic RNA promoters in vivo. Virology 275, 177-192.

Griess et al. (1994) Plant Physiol. 104:1467.

Gruber et al. (1993) Vectors for plant transformation. In: Glick, B. R. and Thompson J. E. (Eds.) Methods in Plant Molecular Biology and Biotechnology, CRC Press, pp. 89-119.

Guerineau et al. (1991) Mol. Gen. Genet. 262:141-144

Guevara-Garcia et al. (1993) Plant J. 4(3): 495-505

Guilley, H., Dudley, R. K., Jonard, G., Balazs, E. and Richards, K. E. (1982) Transcription of Cauliflower mosaic virus DNA: detection of promoter sequences, and characterization of transcripts. Cell 30, 763-773.

Gurley, W. B., Czarnecka, E., Nagao, R. T. and Key, J. L. (1986) Upstream sequences required for efficient expression of a soybean heat shock gene. Mol. Cell. Biol. 6, 559-565.

Hammock et al. 91990) Nature 344:458.

Hansen et al. (1997) *Mol. Gen. Genet.* 254(3):337-343

Hayes et al. (1992) Biochem. J. 285:173

Hiei, Y., Ohta, S., Komari, T. and Kumashiro, T. (1994) Efficient transformation of rice (*Oryza sativs* L.) mediated by *Agrobacterium* and sequence analysis of the boundaries of the T-DNA. Plant J. 6, 271-282.

Higgins, D. G. and Sharp, P. M. (1988) CLUSTAL: a package for performing multiple sequence alignment on a microcomputer. Gene 73, 237-244.

Higgins, D. G. and Sharp, P. M. (1989) Fast and sensitive multiple sequence alignments on a microcomputer. Comput. Appl. Biosci. 5, 151-153.

Huang, X., Miller, W., Schwartz, S, and Hardison, R. C. (1992) Parallelization of a local similarity algorithm. Comput. Appl. Biosci. 8, 155-65.

Huub et al. (1993) Plant Molec. Biol. 21:985.

Innis, M., Gelfand, D., Sninsky, J. and White, T. (1990) PCR Protocols: A Guide to Methods and Applications. Academic Press, New York.

Innis, M., Gelfand, D. and Sninsky, J. (1995) PCR Strategies. Academic Press, New York.

Innis, M., Gelfand, D. and Sninsky, J. (1999) PCR Applications: Protocols for Functional Genomics. Academic Press, New York.

Ishida, Y., Saito, H., Ohta, S., Hiei, Y., Komari, T. and Kumashiro, T. (1996) High efficiency transformation of maize (*Zea mays* L.) mediated by *Agrobacterium tumefaciens*. Nat. Biotechnol. 14, 745-750.

Jaynes et al. (1993) Plant. Sci. 89:43.

Jefferson, R. A., Kavanagh, T. A. and Bevan, M. W. (1987) GUS fusions: beta-glucuronidase as a sensitive and versatile gene fusion marker in higher plants. EMBO J. 6, 3901-7.

Jobling et al. (1987) Nature 325:622-625

Joshi et al. (1987) Nucleic Acid Res. 15:9627-9639

Kalderon, D., Roberts, B. L., Richardson, W. D. and Smith A. E. (1984) A short amino acid sequence able to specify nuclear location. Cell 39, 499-509.

Karlin, S, and Altschul, S. F. (1990) Methods for assessing the statistical significance of molecular sequence features by using general scoring schemes. Proc. Natl. Acad. Sci. USA 87, 2264-2268.

Karlin, S, and Altschul, S. F. (1993) Applications and statistics for multiple high-scoring segments in molecular sequences. Proc. Natl. Acad. Sci. USA 90, 5873-5877.

Kawalleck et al. (1993) Plant Molec. Biol. 21:673.

Kawamata et al. (1997) Plant Cell Physiol. 38(7): 792-803

Klein, T. M., Arentzen, R., Lewis, P. A. and Fitzpatrick-McElligott, S. (1992) Transformation of microbes, plants and animals by particle bombardment. Biotechnology (N Y) 10, 286-291.

Knultzon et al. (1992) Proc. Nat. Acad. Sci. USA 89:2624.

Kozak, M. (1987) J Mol. Biol. 196:947-950

Kramer et al. (1993) Insect. Molec. Biol. 23:691

Lam (1994) Results Probl. Cell Differ. 20: 181-196; Lee et al. (1988) EMBO J. 7:1241

Lee, N., Wang, Y., Yang, J., Ge, K., Huang, S., Tan, J. and Testa, D. (1991) Efficient transformation and regeneration of rice small cell groups. Proc. Nat. Acad. Sci. USA 88, 6389-6393.

Leung, J., Fukuda, H., Wing, D., Schell, J. and Masterson, R. (1991) Functional analysis of cis-elements, auxin response and early developmental profiles of the mannopine synthase bi-directional promoter. Mol. Gen. Genet. 230, 463-474.

Lommel et al. (1991) Virology 81:382-385.

Longemann et al. (1992) Bio/Technology 10:3305.

Macejak et al. (1991) Nature 353:90-94

MacDonald et al. (1991) Characterization of the polyadenylation signal from the T-DNA-encoded octopine synthase gene 19(20)5575-5581

Maiti, I. B., Gowda, S., Kiernan, J., Ghosh, S. K. and Shepherd, R. J. (1997) Promoter/leader deletion analysis and plant expression vectors with the figwort mosaic virus (FMV) full length transcript (FLt) promoter containing single or double enhancer domains. Transgenic Res. 6, 143-156.

Marshall et al. (1992) Theor. Appl. Genet. 83:435.

Martin et al. (1993) Science 262:1432.

Mathur, J. and Koncz, C. (1998) PEG-mediated protoplast transformation with naked DNA. Methods Mol. Biol. 82, 267-276.

Matsuoka, K. and Nakamura, K. (1991) Propeptide of a precursor to a plant vacuolar protein required for vacuolar targeting. Proc. Natl. Acad. Sci. USA 88, 834-838.

Matsuoka et al. (1993) Proc Natl. Acad. Sci. USA 90(20): 9586-9590

McNellis et al. (1998) Plant J. 14(2):247-257)

Meinkoth, J. and Wahl, G. (1984) Hybridization of nucleic acids immobilized on solid supports. Anal. Biochem. 138, 267-284.

Mett et al. PNAS 90: 4567-4571 (1993)

Mild et al. (1990) Theor. Appl. Genet. 80:449.

Mild et al. (1993) "Procedures for Introducing Foreign DNA into Plants" in *Methods in Plant Molecular Biology and biotechnology* Glick et al. (eds) CRC Press, pp. 67-88.

Mild, B. and McHugh, S. (2004) Selectable marker genes in transgenic plants: applications, alternatives and biosafety. J. Biotechnol. 107, 193-232.

Mindrinos et al. (1994) Cell 78:1089.

Mogen et al. (1990) Plant Cell 2:1261-1272

Moloney, M. et al. (1989) High efficiency transformation of *Brassica napus* using *Agrobacterium* vectors. Plant Cell Reports 8, 238-242.

Mullis et al. (1987) Methods Enzymol. 155:335-350

Munroe et al. (1990) Gene 91:151-158

Murray et al. (1989) Nucleic Acids Res. 17:477-498

Myers, E. W. and Miller, W. (1988) Optimal alignments in linear space. Comput. Appl. Biosci. 4, 11-17.

Needleman, S. B. and Wunsch, C. D. (1970) A general method applicable to the search for similarities in the amino acid sequence of two proteins. J. Mol. Biol. 48, 443-453.

Nellen et al. (1993) TIBS 18:419-423

Odell, J. T., Nagy, F. and Chua, N. H. (1985) Identification of DNA sequences required for activity of the cauliflower mosaic virus 35S promoter. Nature 313, 810-812.

Opsahl-Sorteberg, H-G. et al., "Identification of a 49-bp fragment of the HvLTP2 promoter directing aleruone cell specific expression" Gene 341:49-58 (2004).

Orozco et al. (1993) Plant Mol. Biol. 23(6): 1129-1138

Pang et al. (1992) Gene 116:165.

Pearson, W. R. and Lipman, D. J. (1988) Improved tools for biological sequence comparison. Proc. Natl. Acad. Sci. USA 85, 2444-2448.

Pearson, W. R. (1994) Using the FASTA program to search protein and DNA sequence databases. Methods Mol. Biol. 24, 307-331.

Pen et al. (1992) Bio/Technology 10:292

Poehlman, J. M. and Sleper, D. A. (1995) *Breeding field crops*, 4th Edition, Iowa State University Press.

Pratt et al. (1989) Biochem. Biophys. Res. Comm. 163:1243.

Proudfoot (1991) Cell 64:671-674

Przibilla et al. (1991) Plant Cell 3:169.

Raboy et al. (1990) Maydica 35:383.

Rinehart et al. (1996) *Plant Physiol.* 112(3): 1331-1341

Russell et al. (1997) *Transgenic Res.* 6(2): 157-168

Rogers, J. C. (1985) Two barley alpha-amylase gene families are regulated differently in aleurone cells. J. Biol. Chem. 260, 3731-3738.

Russell, D. A. and Fromm, M. E. (1997) Tissue-specific expression in transgenic maize of four endosperm promoters from maize and rice. Transgenic Res. 6, 157-168.

Sambrook, J., Fritsch, E. F. and Maniatis, T. (1989) Molecular Cloning: A Laboratory Manual, 2nd Edition. Cold Spring Harbor Laboratory Press, Plainview, N. Y.

Sanfacon et al. (1991) Genes Dev. 5:141-149

Schena et al. (1991) Proc. Natl. Acad. Sci. USA 88:10421-10425

Shiroza et al. (1988) J. Bacteriol. 170:810.

Smith, T. F. and Waterman, M. S. (1981) Adv. Appl. Math. 2, 482-489.

Smith et al. (2000) nature 407:319-320

Sogaard et al. (1993) J. Biol. Chem. 268(30)22480-4.

Steinecke et al. (1992) EMBOL J. 11:1525.

Steinmetz et al. (1985) Mol. Gen. Genel. 200:220

Stiefel, V., Ruiz-Avila, L., Raz, R., Pilar Valles, M., Gomez, J., Pages, M., Martinez-Izquierdo, J. A., Ludevid, M. D., Langdale, J. A., Nelson, T., et al. (1990) Expression of a maize cell wall hydroxyproline-rich glycoprotein gene in early leaf and root vascular differentiation. Plant Cell 2, 785-793.

Sumitani et al. (1993) Biosci. Biotech. Biochem. 57:1243

Tavladoraki et al. (1993) nature 266:469

Taylor et al. (1994) Abstract #497, Seventh Int'l Symposium on Molecular Plant-Microbe Interations.

Toubart et al. (1992) Plant J. 2:367.

Van Camp et al. (1996) *Plant Physiol.* 112(2): 525-535.

Van Damme et al. (1994) Plant Molec. Biol. 24:825.

Velten, J. and Schell, J. (1985) Selection-expression plasmid vectors for use in genetic transformation of higher plants. Nucleic Acids Res. 13, 6981-6998.

Wan, Y. and Lemaux, P. G. (1994) Generation of large numbers of independently transformed fertile barley plants. Plant Physiol. 104, 37-48.

Ward et al. Plant Mol. Biol. 22: 361-366 (1993)

Weising, K., Schell, J. and Kahl, G. (1988) Foreign genes in plants: transfer, structure, expression, and applications. Annu. Rev. Genet. 22, 421-477.

Wohlleben, W., Arnold, W., Broer, I., Hillemann, D., Strauch, E. and Puhler, A. (1988) Nucleotide sequence of the phosphinothricin N-acetyltransferase gene from *Streptomyces virochromogenes* Tu494 and its expression in *Nicotiana tabacum*. Gene 70, 25-37.

Wosnick et al. (1987). Gene 60:115.

Yamamoto et al. (1994) Plant Cell Physiol. 35(5): 773-778

Yamamoto et al. (1997) Plant J. 12(2) 255-265

Xia et al. Plant Physiol. (1994) 104:805-806

What is claimed is:

1. An isolated DNA molecule comprising a first regulatory element having promoter activity and comprising a nucleotide sequence selected from the group consisting of the nucleotide sequence of SEQ ID NO: 2 and a nucleotide sequence comprising a functional fragment of the nucleotide sequence set forth in SEQ ID NO: 2, wherein said functional fragment of SEQ ID NO: 2 retains promoter activity, said first regulatory element is operably linked to a nucleotide sequence of interest which is further operably linked to a second regulatory element having polyadenylation activity and selected from the group consisting of the nucleotide sequence of SEQ ID NO: 4 and a nucleotide sequence comprising a functional fragment of the nucleotide sequence set forth in SEQ ID NO: 4, wherein said functional fragment of SEQ ID NO: 4 retains polyadenylation activity, and wherein said nucleotide sequence of interest is heterologous to said first and second regulatory elements.

2. The isolated DNA molecule of claim 1 wherein said first regulatory element comprises SEQ ID NO: 2.

3. The isolated DNA molecule of claim 1 wherein said second regulatory element comprises SEQ ID NO: 4.

4. The isolated DNA molecule of claim 1, wherein said first regulatory element comprises SEQ ID NO: 2 and wherein said second regulatory element comprises SEQ ID NO: 4.

5. An expression cassette comprising the isolated DNA molecule of claim 1.

6. The expression cassette of claim 5, wherein said first regulatory element comprises SEQ ID NO: 2.

7. The expression cassette of claim 5, wherein said second regulatory element comprises SEQ ID NO: 4.

8. The expression cassette of claim 5, wherein said first regulatory element comprises SEQ ID NO: 2 and said second regulatory element comprises SEQ ID NO: 4.

9. A plant cell comprising the expression cassette of claim 5.

10. The plant cell of claim 9, wherein said first regulatory element comprises SEQ ID NO: 2.

11. The plant cell of claim 9, wherein said second regulatory element comprises SEQ ID NO: 4.

12. The plant cell of claim 9, wherein said first regulatory element comprises SEQ ID NO: 2 and said second regulatory element comprises SEQ ID NO: 4.

13. A plant comprising the expression cassette of claim 5.

14. The plant of claim 13, wherein said first regulatory element comprises SEQ ID NO: 2.

15. The plant of claim 13, wherein said second regulatory element comprises SEQ ID NO: 4.

16. The plant of claim 13, wherein said first regulatory element comprises SEQ ID NO: 2 and said second regulatory element comprises SEQ ID NO: 4.

17. A method for expressing a nucleotide sequence of interest in a plant cell, the method comprising:

(a) transforming a plant cell with a DNA molecule comprising a nucleotide sequence comprising a first isolated regulatory element having promoter activity and comprising a nucleotide sequence selected from the group consisting of the nucleotide sequence of SEQ ID NO: 2 and a nucleotide sequence comprising a functional fragment of the nucleotide sequence set forth in SEQ ID NO: 2, wherein said functional fragment of SEQ ID NO: 2 retains promoter activity, said first regulatory element is operably linked to a nucleotide sequence of interest which is further operably linked to a second regulatory element having polyadenylation activity and selected from the group consisting of the nucleotide sequence of SEQ ID NO: 4 and a nucleotide sequence comprising a functional fragment of the nucleotide sequence set forth in SEQ ID NO: 4, and wherein said functional fragment of SEQ ID NO: 4 retains polyadenylation activity, and wherein said nucleotide sequence of interest is heterologous to said first and second regulatory elements; and (b) growing said plant cell to produce a plant expressing said nucleotide sequence of interest.

18. The method of claim 17, wherein said first regulatory element comprises SEQ ID NO: 2.

19. The method of claim 17, wherein said second regulatory element comprises SEQ ID NO: 4.

20. The method of claim 7, wherein said first regulatory element comprises SEQ ID NO: 2 and said second regulatory element comprises SEQ ID NO: 4.

* * * * *